(12) United States Patent
Mansour

(10) Patent No.: US 9,949,876 B2
(45) Date of Patent: Apr. 24, 2018

(54) SMALL GAUGE INSTRUMENTS FOR MICRO SURGERY

(71) Applicant: CYGNUS LP, Roswell, GA (US)

(72) Inventor: Fouad Mansour, Sandy Springs, GA (US)

(73) Assignee: CYGNUS LP, Roswell, GA (US)

( * ) Notice: Subject to any disclaimer, the term of this patent is extended or adjusted under 35 U.S.C. 154(b) by 0 days.

(21) Appl. No.: 14/639,663

(22) Filed: Mar. 5, 2015

(65) Prior Publication Data

US 2015/0342584 A1 Dec. 3, 2015

Related U.S. Application Data

(60) Provisional application No. 61/948,329, filed on Mar. 5, 2014.

(51) Int. Cl.
*A61F 9/007* (2006.01)
*A61B 17/00* (2006.01)
*A61F 9/008* (2006.01)
*A61B 17/34* (2006.01)

(52) U.S. Cl.
CPC ...... *A61F 9/00821* (2013.01); *A61B 17/3421* (2013.01); *A61B 17/3462* (2013.01); *A61F 9/00736* (2013.01); *A61B 2017/00305* (2013.01); *A61B 2017/00477* (2013.01); *A61B 2017/347* (2013.01); *A61B 2017/3443* (2013.01)

(58) Field of Classification Search
CPC ............ A61B 17/3421; A61B 17/3462; A61B 17/00234; A61F 9/00–9/009
USPC ................................................. 606/1, 6, 107
See application file for complete search history.

(56) References Cited

U.S. PATENT DOCUMENTS

| | | | |
|---|---|---|---|
| 4,573,979 A * | 3/1986 | Blake | A61M 1/0084 604/240 |
| 2005/0154379 A1* | 7/2005 | McGowan, Sr. | A61F 9/008 606/4 |
| 2006/0041291 A1* | 2/2006 | Buzawa | A61B 17/3421 607/101 |
| 2012/0245569 A1* | 9/2012 | Papac | A61B 3/102 606/1 |
| 2013/0197488 A1* | 8/2013 | Scheller | A61F 9/00736 606/1 |
| 2014/0180264 A1* | 6/2014 | Diao | A61F 9/00823 606/4 |

* cited by examiner

*Primary Examiner* — Nathan J Jenness
(74) *Attorney, Agent, or Firm* — Baker Hostetler LLP

(57) ABSTRACT

A surgical system combines a cannula and an instrument in a manner that allows small gauge instruments to be used effectively, with little or no bending with respect to the manipulating proximal side of the instrument. Such design overcomes the shortcomings of prior art, and applies to various microsurgical procedures, including ophthalmology, allowing the use of smaller endo-photocoagulation probes, illumination probes, combination probes, vitrectors, scissors, manipulators, picks, diathermy, and others. By using smaller gauge, patient recovery is expected to be faster.

13 Claims, 6 Drawing Sheets

Traditional Design

Traditional Design

Prior Art

Sleeve Reinforced Design

Sleeve Reinforced Design

Prior Art

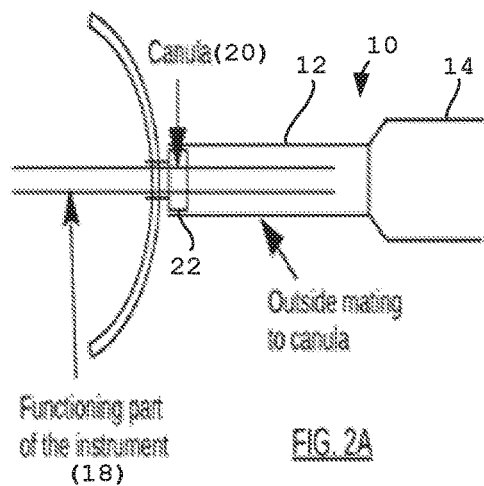
FIG. 2A
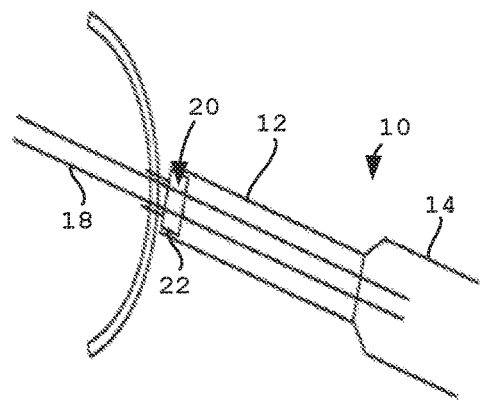
FIG. 2B-Flexed Position
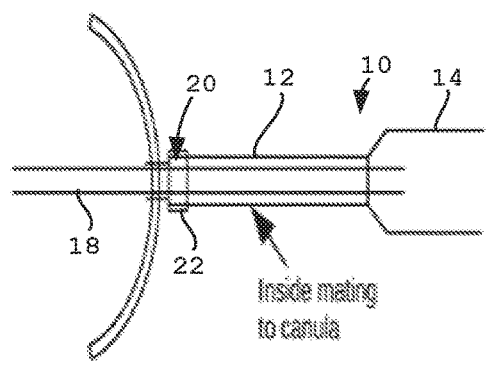
FIG. 2C
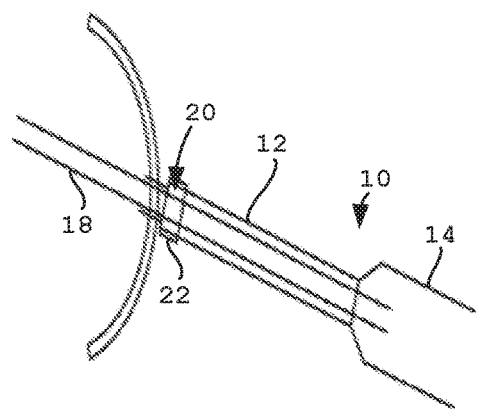
FIG. 2D-Flexed Position
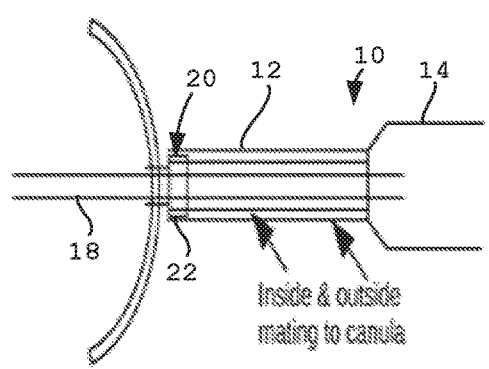
FIG. 2E
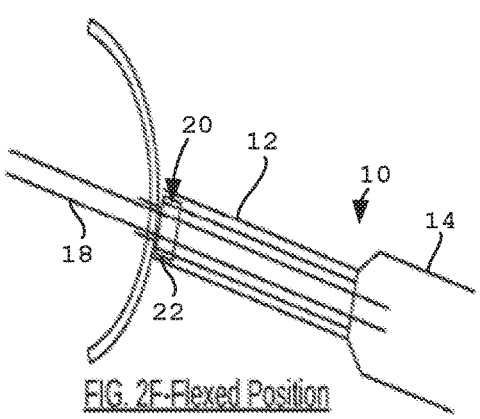
FIG. 2F-Flexed Position

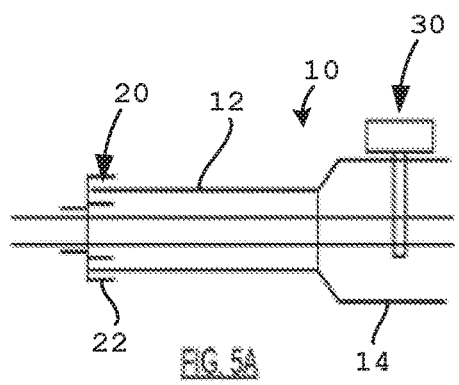
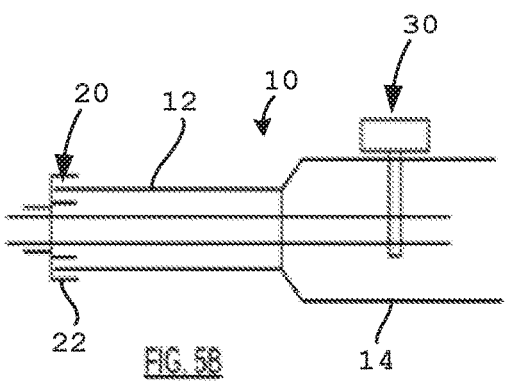
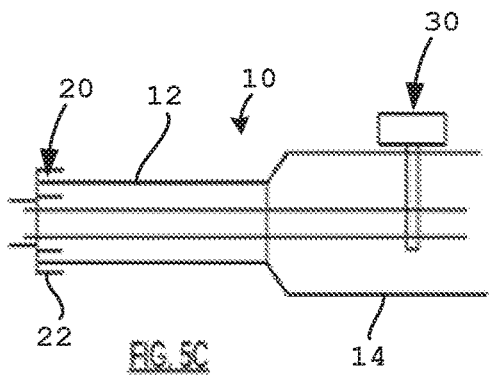
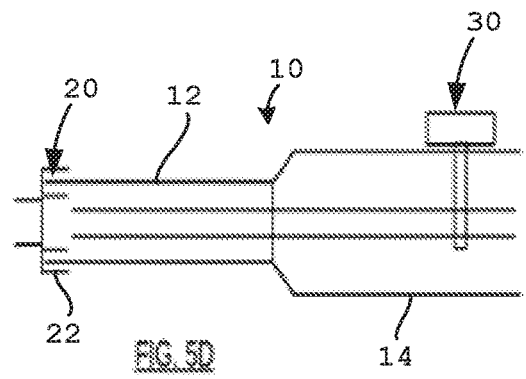

SMALL GAUGE INSTRUMENTS FOR MICRO SURGERY

CROSS-REFERENCE TO RELATED APPLICATIONS

The present United States non-provisional patent application claims priority to, and full benefit of, U.S. provisional patent application Ser. No. 61/948,329, filed on Mar. 5, 2014, entitled "Small Gauge Instruments for Micro Surgery," the disclosure of which is incorporated by reference herein as though set forth in its entirety.

TECHNICAL FIELD

The subject matter of the present invention relates, generally, to reducing the size of instruments that are used in micro surgery; thus, reducing the trauma and recovery time for the patient. In retina surgery, this includes, but is not limited to, laser probes for endo-photocoagulation, illumination probes used in the vitreous, vitrectors, instruments (knives, scissors, manipulators, picks, and the like), multi-function probes, diathermy, and the like. In other applications, electrodes for sensing and/or delivering energy are included.

BACKGROUND

In the field of endo-photocoagulation laser treatment at the retina during eye surgery, it is desirable to reduce the size of the entry site in order to have less trauma and recovery time for the patient.

Most often, and as in other fields is medical surgery, a trocar system is used, whereby a cannula is inserted at the entry site with the assistance of a puncturing device/instrument. Once the cannula is in place, the puncturing device/instrument is withdrawn and the cannula serves as an opening that allows one or more device to enter through the cannula and into the surgical site where it is needed.

As the industry has moved toward smaller diameters (typically, 27 gauge, 25 gauge, and 23 gauge, as opposed to the larger, 20 gauge), such current systems prove to have engineering limitations, as the small gauge instruments tend to flex at the entry point when the direction of the instrument (generally via a hand held instrument base) is changed in order to target other areas in the general proximity.

As the outside diameter of the cannula is always larger than the outside diameter of the device to be inserted therethrough, it is important to note that a 25 gauge instrument will use close to 23.5 gauge cannula, and a 23 gauge instrument will use close to 21.5 gauge cannula.

In practice, with the 23 gauge system, the entry wound diameter is reduced by about 15%, and for the 25 gauge system, it is reduced by about 33%, in comparison with the 20 gauge system.

With the 25 gauge system, the flexibility of the instruments reached an upper limit that not all surgeons are comfortable with, opting instead for the larger 23 gauge system.

As for the 27 gauge system, the flexibility is reduced by using a reinforcing sleeve that stays close to the cannula entry, using the physics of a cantilever, where rigidity is the strongest at the base (or lateral movement is the lowest) compared to the distal end, as in the case of U.S. patent application Ser. No. 11/268,928.

Such size and technique provides very little control over changing the direction of the instrument and is used only in very simple operation where the target area is very small.

Hence, a new approach is needed in order to use smaller gauge instruments, increasing the level of manipulation by the surgeon, with the least amount of sacrifice in performance.

SUMMARY

In recognition of the above-described problems, a solution is herein proposed. With the decrease in instrument sizes, stiffening of the instruments becomes more challenging, with the current state of the art. It becomes more convenient that the instrument relies primarily on the rigidity of the cannula itself, by anchoring the instrument to the cannula.

As the cannula is typically around 4 mm long, bending it is not practically possible, even at smaller sizes.

The advantage of such new approach allows for smaller cannulas and, thus, smaller instruments to be inserted through such cannulas, while maintaining similar control that is comparable to larger size instruments when restricted to the current state of the art.

As an illustration, a 34 gauge tube can fit a 100 micron laser fiber, and such a tube can go through a 30 gauge cannula; thus, reducing the entry wound diameter by about 66% when compared to 20 gauge cannulas, 60% when compared to 23 gauge cannulas, and 50% when compared to 25 gauge cannulas, and still with minimal compromise to the effectiveness and maneuvering offered by the 20 gauge system that is restricted to the current state of the art.

In a first embodiment, the cannula is geometrically similar to what is currently used, while the instrument mates at the base of the cannula, at the external surface of the cannula entry point.

In such arrangement, the instrument diameter connecting to the cannula is chosen so that it has a diameter that resists flexing, allowing the cannula to change direction independently of the instrument flexibility. Such instrument size would be typically 20 gauge or larger. Once the instrument is engaged at the base of the cannula, the functioning (and smaller) part of the instrument passes through the cannula and into the surgical spot.

In some cases, the functioning part of the instrument may enter through the cannula prior to mating the instrument and cannula.

However, having a short instrument length allows for smaller instrument size, as the flexing would diminish. In case of longer instruments, a larger instrument size may be needed.

As the instrument is manipulated laterally at its handle, the attached large gauge part of the instrument connecting to the cannula moves into the desired position, and if needed, the functioning part of the instrument is allowed to move in and out of the surgical spot using secondary manipulation at the instrument.

In a second embodiment, the cannula is geometrically similar to what is currently used, with the difference being that the instrument mates at the base of the cannula at the internal surface of the cannula entry point.

In a third embodiment, the cannula is geometrically similar to what is currently used, with the difference being that the instrument mates at the base of the cannula at the internal and external surfaces of the cannula entry point.

These and other features and advantages of the various embodiments of devices and related systems, as set forth within the present disclosure, will become more apparent to those of ordinary skill in the art after reading the following Detailed Description of Illustrative Embodiments and the Claims in light of the accompanying drawing Figures.

BRIEF DESCRIPTION OF THE DRAWINGS

Accordingly, the within disclosure will be best understood through consideration of, and with reference to, the following drawing Figures, viewed in conjunction with the Detailed Description of Illustrative Embodiments referring thereto, in which like reference numbers throughout the various Figures designate like structure, and in which:

FIG. 2A illustrates the first embodiment of the present invention in the straight position;

FIG. 2B illustrates the first embodiment of the present invention in the flexed position;

FIG. 2C illustrates the second embodiment of the present invention in the straight position;

FIG. 2D illustrates the second embodiment of the present invention in the flexed position;

FIG. 2E illustrates the third embodiment of the present invention in the straight position;

FIG. 2F illustrates the third embodiment of the present invention in the flexed position;

FIG. 5A illustrates deployment (when needed) of the functioning part of the instrument for the third embodiment of the present invention;

FIG. 5B illustrates the retraction (when needed) of the functioning part of the instrument for the third embodiment (past the cannula) of the present invention;

FIG. 5C illustrates an optional retraction (when needed) of the functioning part of the instrument for the third embodiment (within and including the edges of the cannula) of the present invention; and FIG. 5D illustrates another optional retraction (when needed) of the functioning part of the instrument for the third embodiment (not reaching the cannula) of the present invention.

DETAILED DESCRIPTION OF ILLUSTRATIVE EMBODIMENTS

Figure 1A:
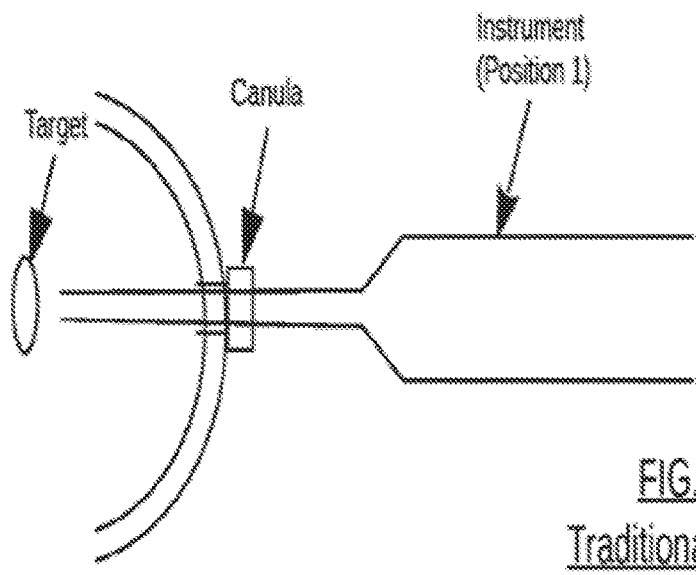
FIG. 1A illustrates a representative of the traditional design, prior art in a straight position.

In describing the several embodiments illustrated in the Figures, specific terminology is employed for the sake of clarity. The invention, however, is not intended to be limited to the specific terminology so selected, and it is to be understood that each specific element includes all technical equivalents that operate in a similar manner to accomplish a similar purpose. Additionally, in the Figures, like reference numerals shall be used to designate corresponding parts throughout the several Figures.

Figure 1B:
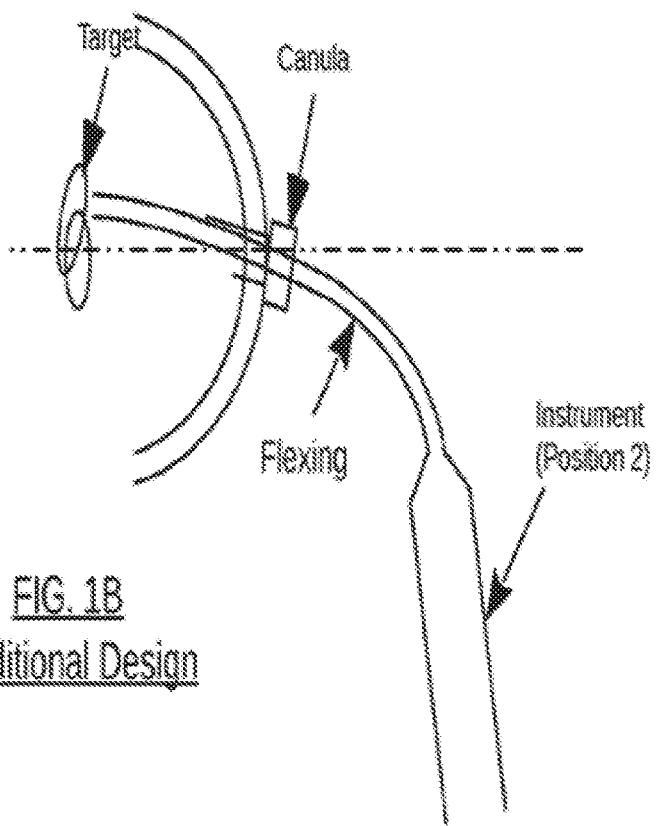
FIG. 1B illustrates a representative of the traditional design, prior art in a flexed position.

As illustrated in FIGS. 1A-1B, a representative, prior art shows the typical functioning of an instrument through a cannula.

In order to target an adjacent area, the instrument is manipulated by changing the angle. The smaller the instrument, the more flexing is observed.

Depending on the instrument, a certain flexing cannot be exceeded without compromising its function.

Figure 1C:
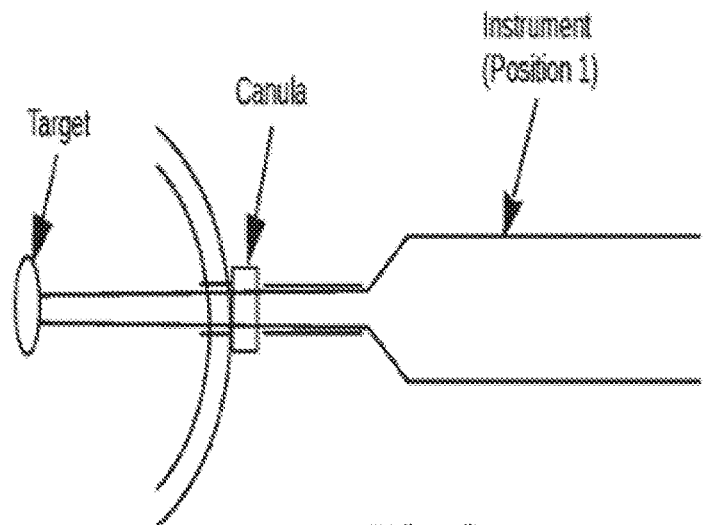
FIG. 1C illustrates a representative of the sleeve reinforced design, prior art in a straight position.
Figure 1D:
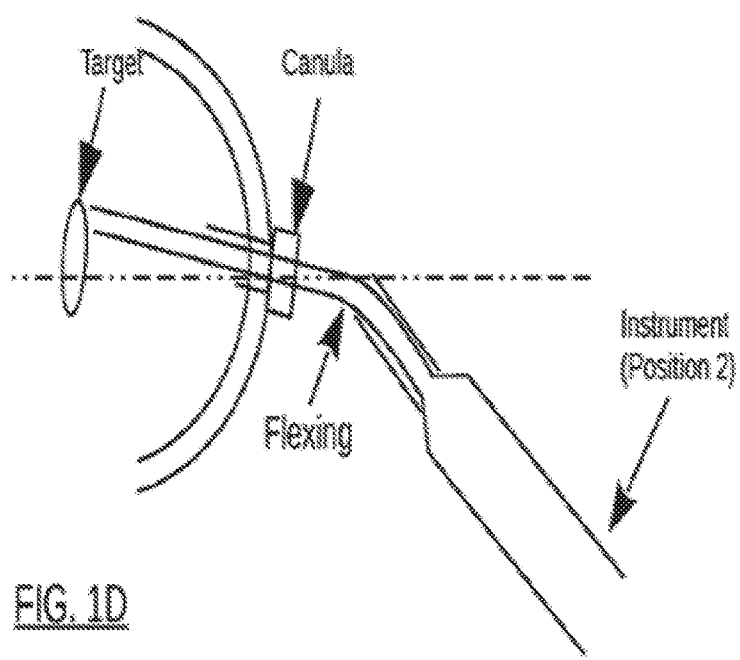
FIG. 1D illustrates a representative of the sleeve reinforced design, prior art in a flexed position.
Figure 3A:
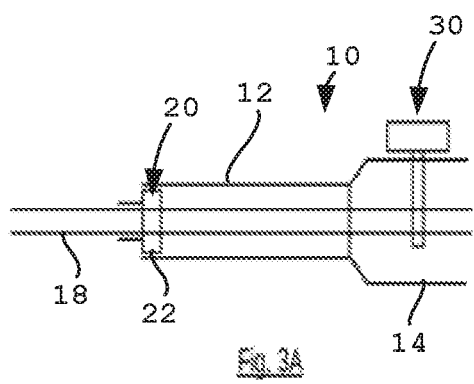
FIG. 3A illustrates deployment (when needed) of the functioning part of the instrument for the first embodiment of the present invention.
Figure 3B:
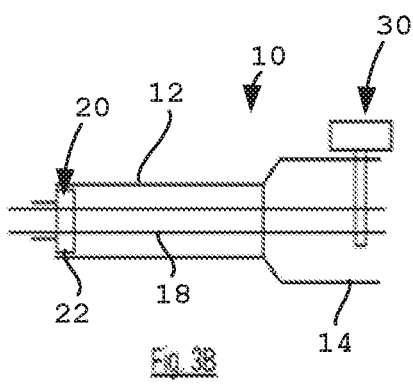
FIG. 3B illustrates the retraction (when needed) of the functioning part of the instrument for the first embodiment (past the cannula) of the present invention.
Figure 3C:
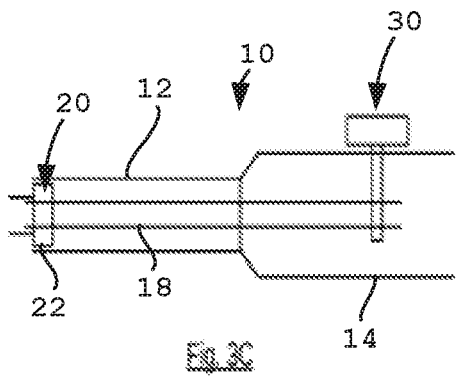
FIG. 3C illustrates an optional retraction (when needed) of the functioning part of the instrument for the first embodiment (within and including the edges of the cannula) of the present invention.
Figure 3D:
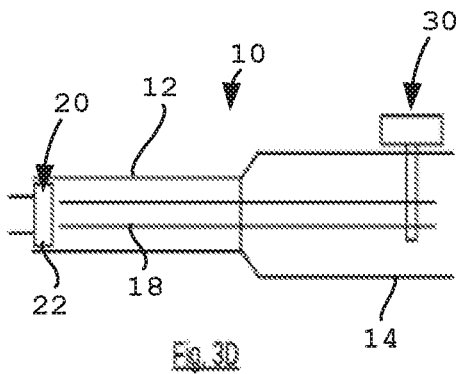
FIG. 3D illustrates another optional retraction (when needed) of the functioning part of the instrument for the first embodiment (not reaching the cannula) of the present invention.
Figure 4A:
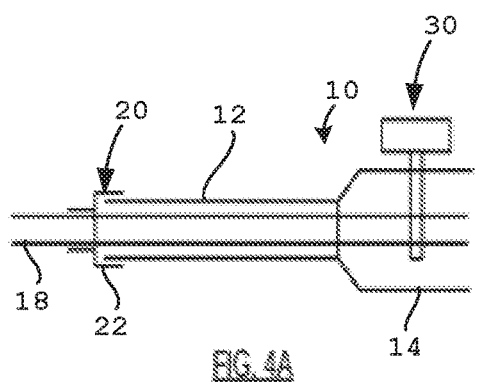
FIG. 4A illustrates deployment (when needed) of the functioning part of the instrument for the second embodiment of the present invention.
Figure 4B:
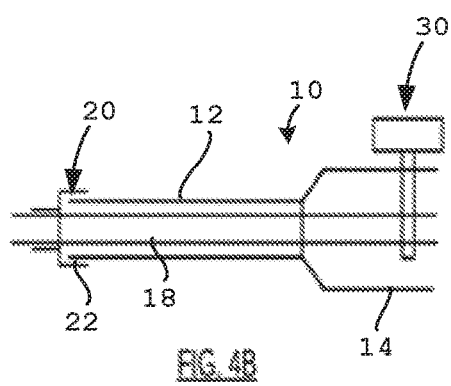
FIG. 4B illustrates the retraction (when needed) of the functioning part of the instrument for the second embodiment (past the cannula) of the present invention.
Figure 4C:
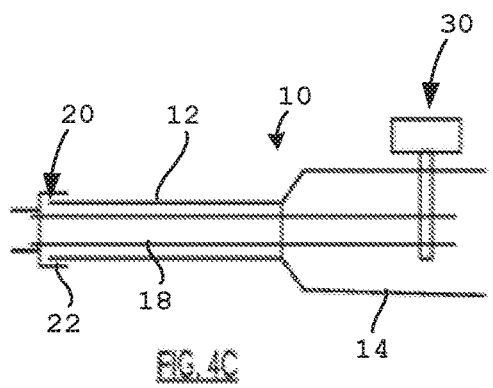
FIG. 4C illustrates an optional retraction (when needed) of the functioning part of the instrument for the second embodiment (within and including the edges of the cannula) of the present invention.
Figure 4D:
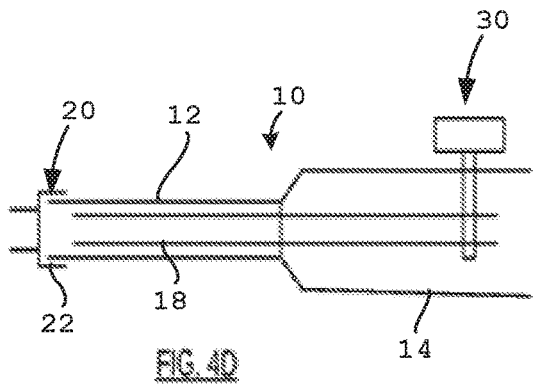
FIG. 4D illustrates another optional retraction (when needed) of the functioning part of the instrument for the second embodiment (not reaching the cannula) of the present invention.

The smaller diameters clearly show an increasing challenge to effectively use the instrument As illustrated in FIGS. 1C-1D, representative illustrations of the prior art show the typical functioning of an instrument through a cannula, using a sleeve reinforcement to limit the flexing.

As in FIGS. 1A-1B, flexing is still occurring between the base of the cannula and the instrument.

In this design, flexing is reduced; thus, allowing the use of smaller instruments.

Such a design has its limitation, as smaller instruments will bend sharply at the base of the cannula, risking catastrophic failure, including but not limited to instrument failure or breakage of a fiber optic caused by excessive bending.

Turning now to a discussion of the inventive aspects of the present disclosure, and as illustrated in FIGS. 2A-2B, a large sleeve 12 surrounds and mates with the base 22 of the cannula 20 on the outside.

Manipulating the handle 14 of the instrument 10 causes the short cannula 20 to reshape the entry location, without any stress or bending on the functioning part 18 of the instrument 10.

As illustrated in FIGS. 2C-2D, a large sleeve 12 is inserted and mates with the base 22 of the cannula 20 on the inside.

Manipulating the instrument 10 causes the short cannula 20 to reshape the entry location, without any stress or bending on the functioning part 18 of the instrument 10.

As illustrated in FIGS. 2E-2F, a large sleeve 12 surrounds the wall of the base 22 of the cannula 20 and mates with the base 22 of the cannula 20 on the inside and outside.

Manipulating the instrument 10 causes the short cannula 20 to reshape the entry location, without any stress or bending on the functioning part 18 of the instrument 10.

As illustrated in FIGS. 3A-3D, the functioning part 18 of the instrument 10 can be deployed using a mechanical mechanism 30 that advances it into the desired surgical position. In the fully retracted position, the tip of the functioning part 18 of the instrument 10 may be beyond the distal end of the cannula 20, within the cannula 20, or prior to the proximal part of the cannula 20. These illustrations pertain to a first embodiment.

As illustrated in FIGS. 4A-4D, the functioning part 18 of the instrument 10 can be deployed using a mechanical mechanism 30 that advances it into the desired surgical position. In the fully retracted position, the tip of the functioning part 18 of the instrument 10 may be beyond the distal end of the cannula 20, within the cannula 20, or prior to the proximal part of the cannula 20. These illustrations pertain to a second embodiment.

As illustrated in FIGS. 5A-5D, the functioning part 18 of the instrument 10 can be deployed using a mechanical mechanism 30 that advances it into the desired surgical position. In the fully retracted position, the tip of the functioning part 18 of the instrument 10 may be beyond the distal end of the cannula 20, within the cannula 20, or prior to the proximal part of the cannula 20. These illustrations pertain to the third embodiment.

Having, thus, described exemplary embodiments of the subject matter of the present disclosure, it is noted that the within disclosures are exemplary only and that various other alternatives, adaptations, and modifications may be made within the scope and spirit of the present invention. Accordingly, the present subject matter is not limited to the specific embodiments as illustrated herein, but is only limited by the following claims.

What is claimed:

1. A surgical instrument comprising:
   a handle;
   a cannula configured with a base having an outer diameter larger than an outer diameter of a remainder of the cannula, wherein the cannula is adapted to be inserted into and held at an entry site of an eye during a micro-surgical procedure;
   a sleeve attached to the handle and adapted to selectively anchor with the base of the cannula after the cannula is inserted into and held at the entry site of the eye during the micro-surgical procedure, wherein the sleeve surrounds an outer circumferential surface of the base of the cannula when anchored with the base of the cannula; and
   an elongate functioning member extending from the handle and associated with the sleeve, the functioning member adapted to be inserted through the cannula after the cannula is inserted into and held at the entry site of the eye during the micro-surgical procedure,
   wherein the sleeve and the cannula, when anchored, at least reduce bending of the functioning member during manipulation of the surgical instrument.

2. The surgical instrument of claim 1, wherein the functioning member is at least partially disposed within the sleeve.

3. The surgical instrument of claim 1, further comprising:
   a mechanical mechanism extending at least partially external to the handle and connected, within the handle, to the functioning member, the mechanical mechanism adapted to advance or retract the functioning member through the cannula during the micro-surgical procedure.

4. The surgical instrument of claim 2, wherein the numerical value of the gauge of the sleeve is 20 gauge or less.

5. The surgical instrument of claim 1, wherein a distance, along the sleeve, between the handle and the base of the cannula at the time that the sleeve is anchored to the base of the cannula is equal to a distance, along the sleeve, between the handle and the base of the cannula at the time that the elongate functioning member is inserted through the cannula.

6. The surgical instrument of claim 1, wherein the sleeve is fixedly attached to an end portion of the handle, wherein the end portion of the handle is proximate to the entry site of the eye relative to a second distal portion of the handle.

7. The surgical instrument of claim 1, wherein the base of the cannula is configured to abut an outer surface of the eye when the cannula is held at the entry site of the eye.

8. A method of anchoring a surgical instrument to a cannula for use during a micro-surgical procedure, the method comprising:
   inserting the cannula into an entry site of an eye during the micro-surgical procedure, wherein the cannula is held at the entry site of the eye during the micro-surgical procedure;
   responsive to inserting the cannula into the entry site of the eye during the micro-surgical procedure, anchoring a sleeve attached to a handle of the surgical instrument to a base of the cannula, wherein the sleeve surrounds an outer circumferential surface of the base of the cannula when anchored with the base of the cannula; and
   inserting a functioning member, extending from the handle and associated with the sleeve, through the cannula to effectuate the micro-surgical procedure.

9. The method of claim 8, wherein the functioning member is at least partially disposed within the sleeve.

10. The method of claim 9, wherein the sleeve is anchored to the base of the cannula at an inner circumferential surface of the base of the cannula in addition to the outer circumferential surface of the base of the cannula.

11. The method of claim 9, wherein the numerical value of the gauge of the sleeve is 20 gauge or less.

12. The method of claim 8, further comprising:
   manipulating the surgical instrument, wherein the anchoring the sleeve and the base of the cannula at least reduce bending of the functioning member during the manipulation.

13. The method of claim 8, further comprising:
   manipulating a mechanical mechanism extending at least partially external to the handle and connected, within the handle, to the functioning member to advance or retract the functioning member through the cannula.

* * * * *